United States Patent
Ozasa et al.

(10) Patent No.: US 8,772,738 B2
(45) Date of Patent: Jul. 8, 2014

(54) PARTICLE ANALYZING APPARATUS AND PARTICLE IMAGING METHOD

(75) Inventors: Masatsugu Ozasa, Kobe (JP); Hiroyuki Kobayashi, Kobe (JP)

(73) Assignee: Sysmex Corporation (JP)

( * ) Notice: Subject to any disclaimer, the term of this patent is extended or adjusted under 35 U.S.C. 154(b) by 324 days.

(21) Appl. No.: 12/951,779

(22) Filed: Nov. 22, 2010

(65) Prior Publication Data

US 2011/0127444 A1 Jun. 2, 2011

(30) Foreign Application Priority Data

Nov. 30, 2009 (JP) ................................. 2009-272974
Sep. 6, 2010 (JP) ................................. 2010-198593

(51) Int. Cl.
- *G01N 21/64* (2006.01)
- *G01N 15/14* (2006.01)
- *G01N 15/00* (2006.01)
- *G01N 1/31* (2006.01)

(52) U.S. Cl.
CPC .... *G01N 15/1475* (2013.01); *G01N 2015/0092* (2013.01); *G01N 1/31* (2013.01); *G01N 2015/1438* (2013.01); *G01N 15/147* (2013.01)
USPC ................... 250/458.1; 250/459.1; 250/461.1

(58) Field of Classification Search
USPC ................. 250/458.1, 459.1, 461.1
See application file for complete search history.

(56) References Cited

U.S. PATENT DOCUMENTS

| | | | | |
|---|---|---|---|---|
| 5,260,764 A * | 11/1993 | Fukuda et al. | ................... | 356/73 |
| 5,548,395 A | 8/1996 | Kosaka | | |
| 5,831,723 A * | 11/1998 | Kubota et al. | ................... | 356/73 |
| 6,133,995 A | 10/2000 | Kubota | | |
| 6,317,511 B1 | 11/2001 | Horiuchi | ....................... | 382/133 |
| 6,592,822 B1 * | 7/2003 | Chandler | ................... | 422/82.05 |
| 7,417,734 B2 * | 8/2008 | Kanda | ........................... | 356/337 |
| 7,715,006 B2 | 5/2010 | Tabata | | |
| 8,009,189 B2 * | 8/2011 | Ortyn et al. | ..................... | 348/80 |
| 2002/0018211 A1 * | 2/2002 | Megerle | ....................... | 356/440 |

* cited by examiner

*Primary Examiner* — Christine Sung
(74) *Attorney, Agent, or Firm* — Brinks Gilson & Lione

(57) ABSTRACT

A particle analyzing apparatus, comprising: a flow cell which forms a specimen flow including particles; first and second light sources; an irradiation optical system which applies lights emitted from the first and second light sources so that the lights are applied to the specimen flow; a detector which detects forward scattered light, the forward scattered light being emitted from the first light and scattered by the particle in the specimen flow, and generates a signal according to the detected scattered light; a light blocking member disposed between the flow cell and the detector; a controller which obtains characteristic parameters of the particle based on the signal from the detector; and an imaging device which captures an image of the particle in the specimen flow using the light from the second light source is disclosed. Particle imaging method is also disclosed.

14 Claims, 12 Drawing Sheets

PARTICLE ANALYZING APPARATUS AND PARTICLE IMAGING METHOD

RELATED APPLICATIONS

This application claims priority under 35 U.S.C. §119 to Japanese Patent Application Nos. 2009-272974 filed on Nov. 30, 2009 and 2010-198593 filed on Sep. 6, 2010, the entire contents of which are hereby incorporated by reference.

BACKGROUND OF THE INVENTION

1. Field of the Invention

The present invention relates to a particle analyzing apparatus which applies light to a measurement specimen including particles flowing in a flow cell to analyze the particles using lights generated from the particles in the specimen and particle imaging method.

2. Background Art

The U.S. Pat. No. 6,133,995 discloses a particle measuring apparatus provided with a sheath flow cell which forms a specimen flow including particles enveloped by a sheath liquid, a continuum source and a pulse light source which respectively apply lights to the specimen flow, a detector which detects forward scattered light and fluorescent light generated from the particle on which the light is applied by the continuum source, and a video camera which captures an image of the particle illuminated by the light emitted from the pulse light source, wherein characteristic parameters of the particle are obtained based on signals of the forward scattered light and fluorescent light detected by the detector.

In the particle measuring apparatus, the lights respectively emitted from the continuum source and the pulse light source are applied so that they are orthogonal to each other relative to the sheath flow cell. In the particle measuring apparatus, the light from the continuum source is applied to the particle on the upstream side of the flow cell, and the light from the pulse light source is applied to the particle on the downstream side of the flow cell.

The particle measuring apparatus has a problem that its image contrast is poor in the case where the particle to be imaged is an optically transparent particle, for example, a cell.

SUMMARY OF THE INVENTION

The scope of the invention is defined solely by the appended claims, and is not affected to any degree by the statements within this summary.

A first aspect of the presented invention is a particle analyzing apparatus, comprising: a flow cell which forms a specimen flow including particles; first and second light sources; an irradiation optical system which applies first light emitted from the first light source and second light emitted from the second light source onto the specimen flow; a detector which detects forward scattered light caused by irradiation of the first light onto the particles in the specimen flow, and generates a signal according to the detected forward scattered light; a light blocking member disposed between the flow cell and the detector; a controller which obtains characteristic parameters of the particles based on the signals from the detector; and an imaging device which captures images of the particles in the specimen flow using the second light, wherein the light blocking member is disposed so as to block a direct ray of the first light entering into the detector and block at least a part of a direct ray of the second light entering into the imaging device.

A second aspect of the presented invention is a particle imaging method, comprising: forming a specimen flow including particles in a flow cell; applying first light emitted from first light source and second light emitted from second light source on the specimen flow using an irradiation optical system; detecting, by using a detector, forward scattered light caused by irradiation of the first light onto the particles in the specimen flow in a state where a direct ray of the first light entering into the detector is blocked by a light blocking member; obtaining characteristic parameters of the particles based on the detected forward scattered light; and capturing, by using a imaging device, images of the particles in the specimen flow using the second light in a state where at least a part of a direct ray of the second light entering into the imaging device is blocked by the light blocking member when a particle having a predetermined characteristic parameter is passing through the flow cell.

DETAILED DESCRIPTION OF THE PREFERRED EMBODIMENTS

Hereinafter, a particle analyzing apparatus according to an embodiment of the present invention is described referring to the accompanied drawings. However, the scope of the present invention is not necessarily limited to the particle analyzing apparatus described below.

The particle analyzing apparatus is a cell analyzing apparatus which flows a measurement specimen including cells collected from a patient into a flow cell and applies laser light to the specimen flowing in the flow cell to detect and analyze lights generated from the specimen (for example, forward scattered light, side fluorescent light) to thereby determine whether a cancer cell or an atypical cell (hereinafter, called "abnormal cell") is included in the cell. More specifically, the cell analyzing apparatus is used in a uterocervical cancer screening test in which epithelial cells are examined.

[Overall Structure of Cell Analyzing Apparatus]

Figure 1:
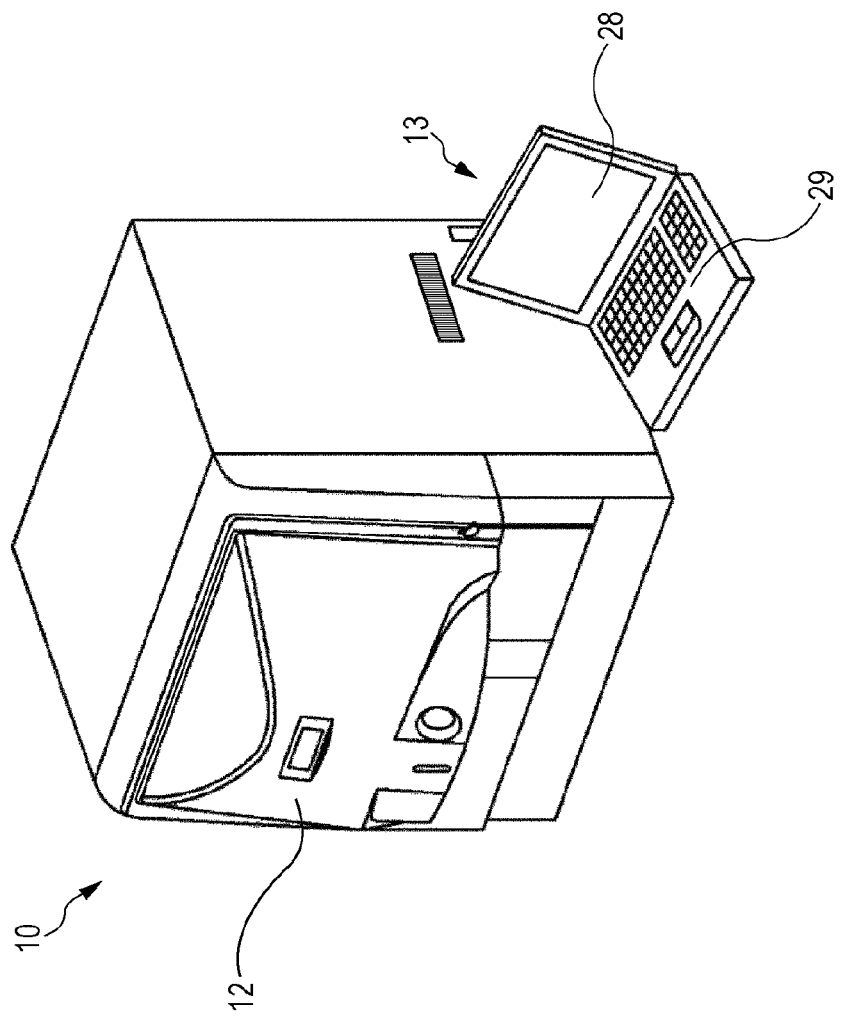
FIG. 1 is a perspective view of a cell analyzing apparatus according to an embodiment of the present invention.

FIG. 1 is a perspective view of a cell analyzing apparatus 10. The cell analyzing apparatus 10 has an apparatus body 12 which measures a specimen, and a system controller 13 connected to the apparatus body 12 to analyze a measurement result thereby obtained.

Figure 2:
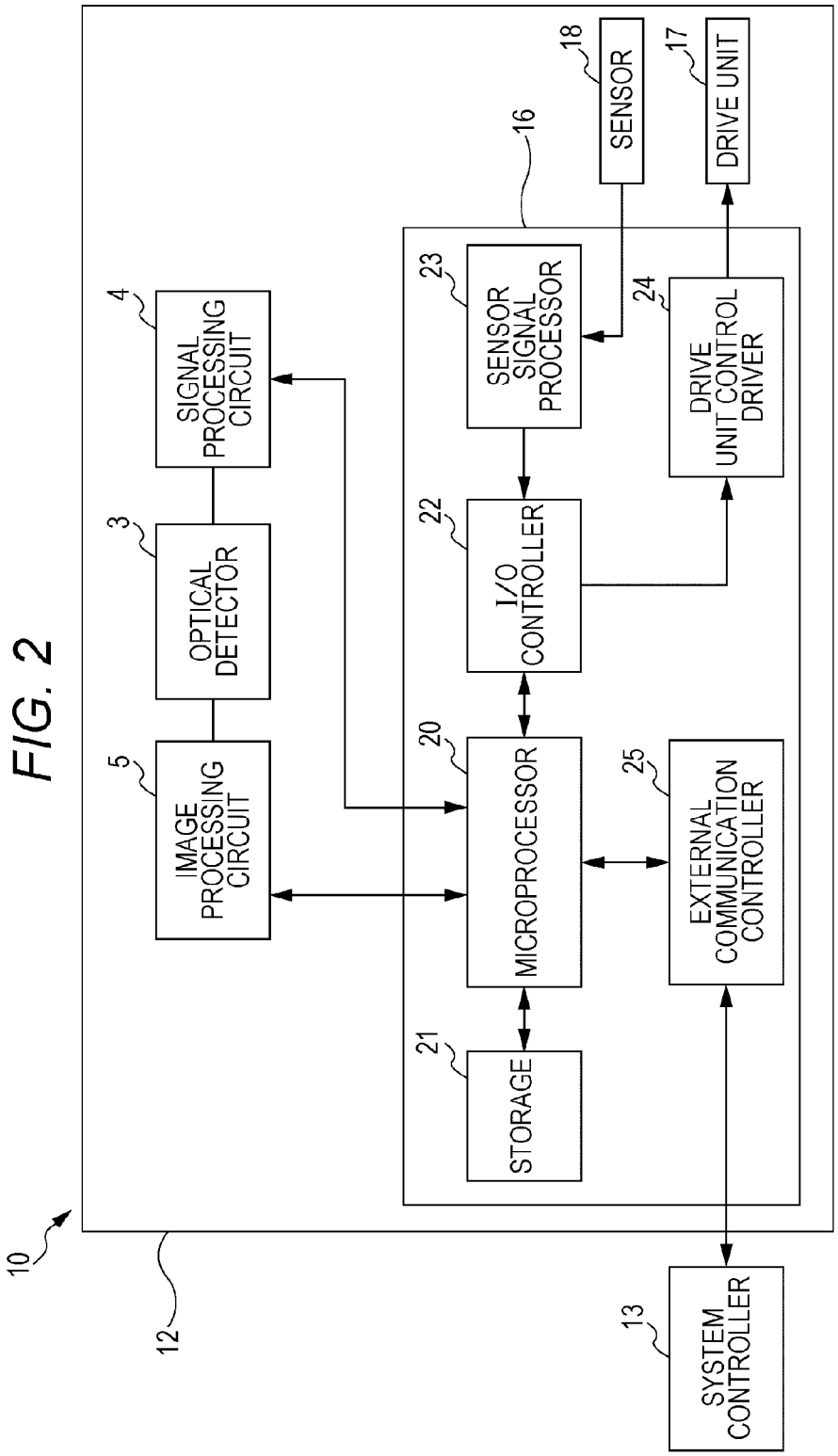
FIG. 2 is a block diagram illustrating structural elements of the cell analyzing apparatus according to the embodiment.

FIG. 2 is a block diagram illustrating structural elements of the cell analyzing apparatus 10. As illustrated in FIG. 2, the apparatus body 12 of the cell analyzing apparatus 10 is provided with an optical detector 3 which detects information, such as cell and nucleus sizes, from the measurement specimen to capture an image of the cell, a signal processing circuit 4, an image processing circuit 5, a measurement controller 16, a drive unit 17 including, for example, a motor, an actuator, and a valve, and various sensors 18. The signal processing circuit 4 includes an analog signal processing circuit which amplifies and filters an output of the optical detector 3 amplified beforehand by a preamplifier (not illustrated in the drawing), an A/D converter which converts an output of the analog signal processing circuit into a digital signal, and a digital signal processing circuit which applies a predetermined waveform process to the digital signal.

When the measurement controller 16 controls the operation of the drive unit 17 while processing the signals outputted from the sensors 18, the measurement specimen is suctioned and measured. The measurement specimen used in the uterocervical cancer screening test can be prepared by performing conventional processes such as centrifugation (thickening), attenuation, agitation, and PI staining, to cells (epithelial cells) collected from the uterine cervix of a patient (test subject). The measurement specimen thus prepared is put in a test tube, and the test tube is placed at a position beneath a pipette (not illustrated in the drawing) of the apparatus body 12. The specimen is then suctioned by the pipette and supplied into the flow cell along with a sheath liquid so that a specimen flow is formed in the flow cell. The PI staining uses propidium iodide (PI) which is a fluorescent staining solution containing dyestuff. The PI staining in which nucleus is selectively stained enables fluorescence detection of the nucleus.

[Structure of Measurement Controller]

The measurement controller 16 has a microprocessor 20, a storage 21, an I/O controller 22, a sensor signal processor 23, a drive unit control driver 24, and an external communication controller 25. The storage 21 includes, for example, ROM and RAM. The ROM stores therein a control program used to control the drive unit 17, and data necessary to run the control program. The microprocessor 20 can load the control program into the RAM to run the control program, or directly run the control program from the ROM.

The microprocessor 20 receives signals transmitted from the sensors 18 by way of the sensor signal processor 23 and the I/O controller 22. By running the control program, the microprocessor 20 can control the drive unit 17 based on the signals outputted from the sensors 18 by way of the I/O controller 22 and the drive unit control driver 24.

The data processed by the microprocessor 20, and data required by the microprocessor 20 to process the data are transmitted and received to and from an external apparatus such as the system controller 13 by way of the external communication controller 25.

[Structure of System Controller]

Figure 3:
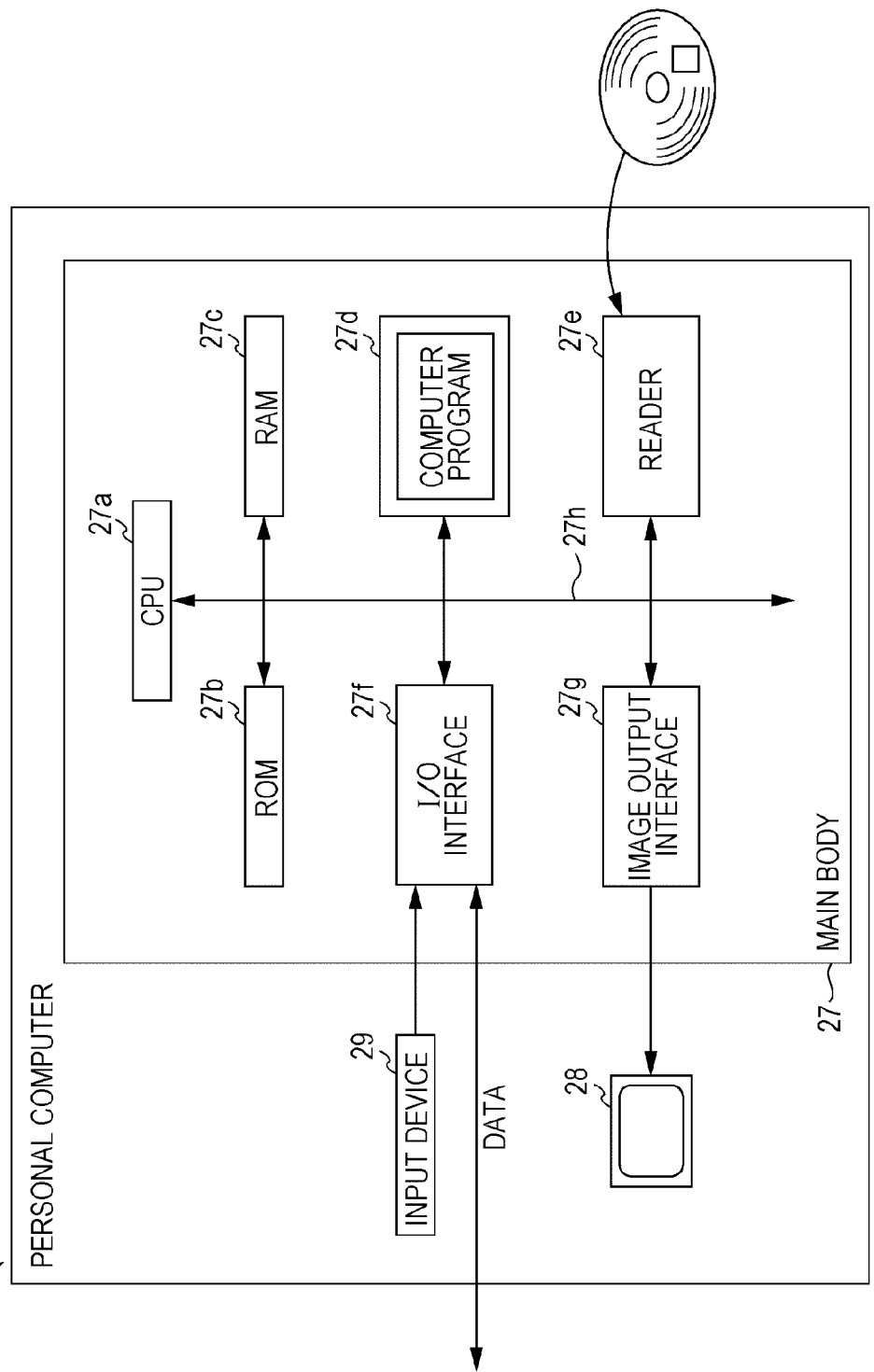
FIG. 3 is a block diagram of a personal computer constituting a system controller according to the embodiment.

FIG. 3 is a block diagram of the system controller 13. The system controller 13 includes, for example, a personal computer, and mainly includes a body 27, a display device 28, and an input device 29. The body 27 includes a CPU 27a, a ROM 27b, a RAM 27c, a hard disc 27d, a readout device 27e, an input/output interface 27f, and an image output interface 27g. These structural elements of the body 27 are connected by a bus 27h so that they can communicate with one another.

The CPU 27a can run computer programs stored in the ROM 27b, and the computer programs loaded into the RAM 27c. The ROM 27b includes, for example, a mask ROM, PROM, EPROM, or EEPROM. The ROM 27b stores therein the computer programs run by the CPU 27a and data used to run the computer programs. The RAM 27c includes, for example, a SRAM or DRAM. The RAM 27c is used to read out the computer programs recorded in the ROM 27b and the hard disc 27d. The RAM 27c is also used as a working region of the CPU 27a when these computer programs are run.

In the hard disc 27d are installed a variety of computer programs to be run by the CPU 27a such as operating system and application programs, and data used to run these computer programs. For example, the operating system providing the graphical user interface environment, such as Windows (registered trademark) manufactured and sold by US Microsoft Co., is installed in the hard disc 27d. In the hard disc 27d are further installed a computer program for discriminating agglutinated particles from non-agglutinated particles and data used to run the computer program.

In the hard disc 27d is further installed an operation program for transmitting a measurement order (operation command) to the measurement controller 16 of the cell analyzing apparatus 10, receiving and processing the measurement result obtained by the apparatus body 12, and displaying the processed analysis result. The operation program is run on the operating system.

The readout device 27e includes a flexible disc drive, CD-ROM drive or DVD-ROM drive. The readout device 27e can read out computer programs or data recorded in a transportable recording medium. The input/output interface 27f includes a serial interface such as USB, IEEE1394, and RS-232C, a parallel interface such as SCSI, IDE, and IEEE1284, and an analog interface such as D/A converter and A/D converter. The input/output interface 27f is connected to the input device 29 including a keyboard and a mouse, and a user can input data to the personal computer by manipulating the input device 29. The input/output interface 27f is also connected to the apparatus body 12 to transmit and receive data to and from the apparatus body 12.

The image output interface 27g is connected to the display device 28 including, for example, LCD or CRT. The image output interface 27g outputs an image signal corresponding to the image data provided from the CPU 27a to the display device 28. The display device 28 displays an image (screen) according to the inputted image signal.

The microprocessor 20 transmit forward scattered light data (FSC), side scattered light data (SSC), and side fluorescent light data (SFL) obtained through signal processes such as filtering and A/D conversion by the signal processing circuit 4, and characteristic parameters obtained from these data which will be described later to the system controller 13 by way of the external communication controller 25. The transmitted data and parameters are then stored in the hard disc 27*d*. The system controller 13 analyzes cells and nucleuses based on the forward scattered light data (FSC), side scattered light data (SSC), side fluorescent light data (SFL), and characteristic parameters. As far as the characteristic parameters of the particle stay within predetermined numeral ranges, a second light source 67, which will be described later, emits light, and a CCD camera 70, which will be described later, captures an image of the particle. Further, a scattergram and a histogram are drawn based on the characteristic parameters, and then displayed.

[Structures of Optical Detector and Imaging Device]

Figure 4:
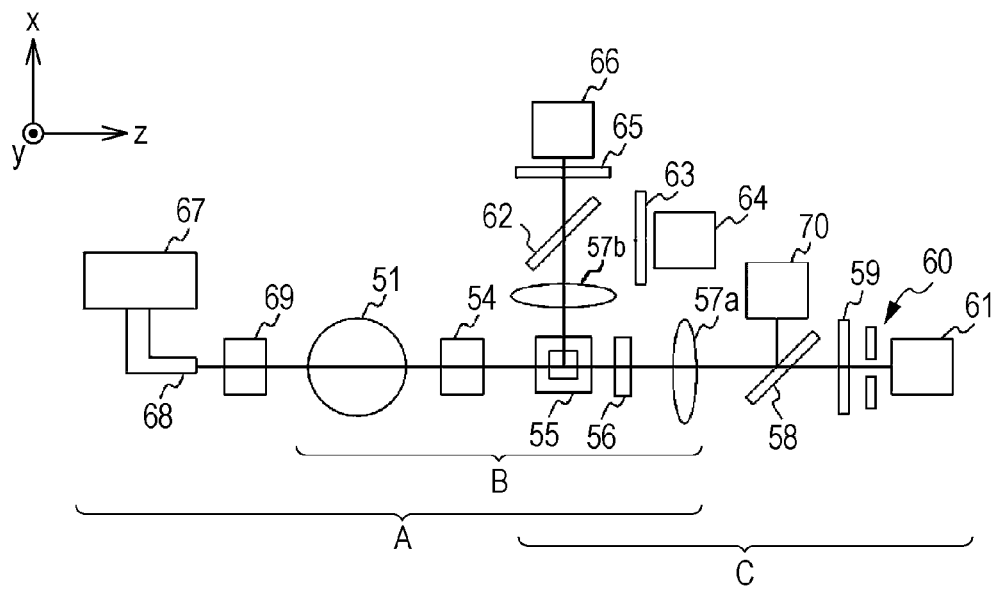
FIG. 4 is a plan view illustrating structural elements of an optical detector according to the embodiment.
Figure 5:
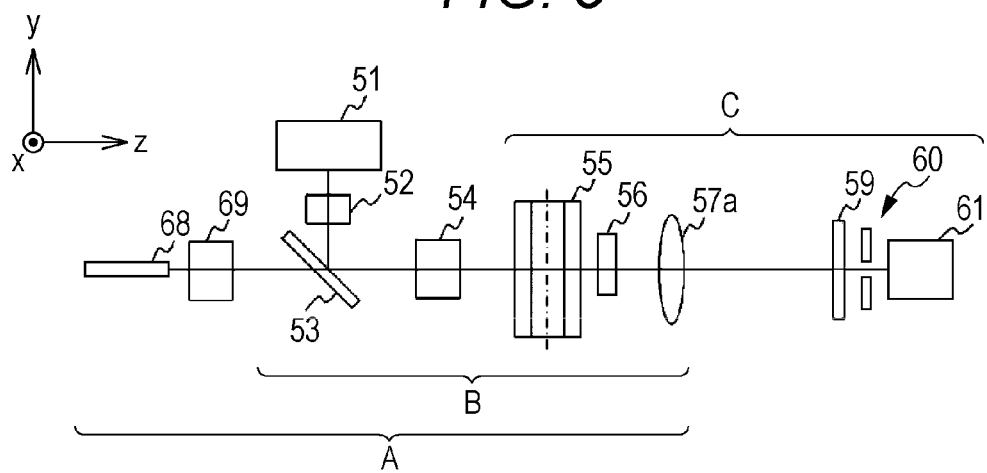
FIG. 5 is a side view illustrating the structural elements of the optical detector according to the embodiment.

FIG. 4 is an upper view of the optical detector 3 (viewed from y direction). FIG. 5 is a side view of the optical detector 3 (viewed from x direction). As illustrated in FIGS. 4 and 5, the optical detector 3 is provided with a first light source 51 including a semiconductor laser. Laser light emitted from the first light source 51 in y direction transmits through a first lens system 52, and is then reflected by a dichroic mirror 53 and concentrated on the measurement specimen flowing in a flow cell 55 through an irradiation lens system 54. The measurement specimen flows in a direction orthogonal to the sheet of paper on which FIG. 4 is printed (y direction). The forward scattered light generated from the cell in the measurement specimen by the laser light emitted from the first light source 51 and applied thereto is detected by a photodiode (detector) 61 by way of a lens 57*a*, a dichroic mirror 58, a filter 59, and a pin hole 60. A group of lenses including a collimeter lens constitute the first lens system 52. A group of lenses including a cylindrical lens constitute a second lens system 69. A light blocking board 56 is provided to block a direct ray coming from the first light source 51.

The side scattered light generated from the cell transmits through a lens 57*b* disposed on a lateral side of the flow cell 55 (in x direction), and is reflected by a dichroic mirror 62, thereafter entering a photomultiplier 64 through a filter 63. Then, the side scattered light generated from the cell is detected by the photomultiplier 64. The side fluorescent light generated from the cell transmits through the lens 57*b* disposed on the lateral side of the flow cell 55 (in x direction) and is reflected by the dichroic mirror 62, thereafter entering a photomultiplier 66 through a filter 65. Then, the side fluorescent light generated from the cell is detected by the photomultiplier 66.

The photodiode 61 and the photomultipliers 64 and 66 convert the detected lights into electrical signals, and respectively output a forward scattered light signal (FSC), a side scattered light signal (SSC), and a side fluorescent light signal (SFL). These signals are amplified by a preamplifier not illustrated in the drawings, and then transmitted to the signal processing circuit 4 described earlier (see FIG. 2).

A gas laser is can be used as the first light source 51 instead of the semiconductor laser, the semiconductor laser is preferably used in view of low cost, compactness, and low power consumption. Thus, the manufacturing cost can be reduced by employing the semiconductor laser, and the apparatus can be miniaturized with less power consumption. The present embodiment uses a blue semiconductor laser having a short wavelength advantageous in narrowing a beam. The blue semiconductor laser is also advantageous for fluorescence exciting wavelength in, for example, PI.

The optical detector 3 further has a second light source 67 including a semiconductor laser which emits a pulse laser light, and a CCD camera 70. The laser light emitted from the pulse laser 67 passes through an optical fiber flux 68, second lens system 69, dichroic mirror 53, and then irradiation lens system 54 to enter the flow cell 55. The laser light then passes through the lens 57*a*, and is reflected by the dichroic mirror 58 to finally form an image in the camera 70. The direct ray coming from the second light source 67 in z direction is blocked by the light blocking board 56. The second light source 67 performs the light emission by a timing by which the camera 70 captures an image of the abnormal cell discriminated based on the characteristic parameters obtained from the forward scattered light data (FSC), side scattered light data (SSC), and side fluorescent light data (SFL).

Though a gas laser can be used in place of the semiconductor laser, the semiconductor laser is preferably used in view of low cost, compactness, and low power consumption. Thus, the manufacturing cost can be reduced by employing the semiconductor laser, and the apparatus can be miniaturized with less power consumption. The present embodiment uses a red semiconductor laser as the second light source 67.

In the case where the lights emitted from the first light source 51 and the second light source 67 are laser lights have an equal wavelength, an additional control becomes necessary, for example, suspension of the continuum emission from the first light source 51 only when the cell image is captured. Therefore, the wavelength of the light emitted from the second light source 67 preferably has a wavelength different to that of the light emitted from the first light source 51. The wavelength of the light emitted from the second light source 67 preferably has a wavelength different to that of the fluorescent light emitted from the particle included in the specimen flow.

As illustrated in FIG. 2, the image of the abnormal cell captured by the camera 70 is transmitted to the system controller 13 via the external communication controller 25 by the image processing circuit 5 and the microprocessor 20. The image of the abnormal cell is stored in the hard disc 27*d* (storage) of the system controller 13 in association with the characteristic parameters obtained from the forward scattered light data (FSC), side scattered light data (SSC), and side fluorescent light data (SFL).

[Description of Optical System]

Figure 6:
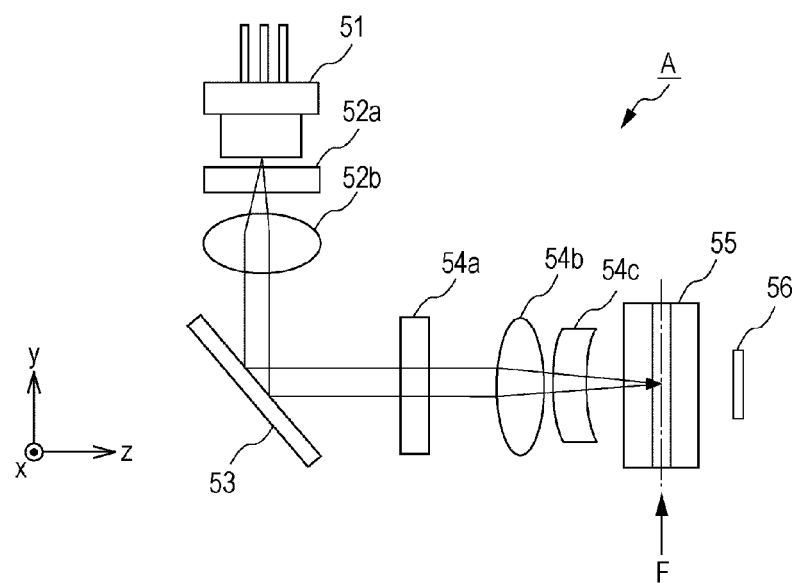
FIG. 6 is a side view of an optical system relating to a first light source according to the embodiment.
Figure 7:
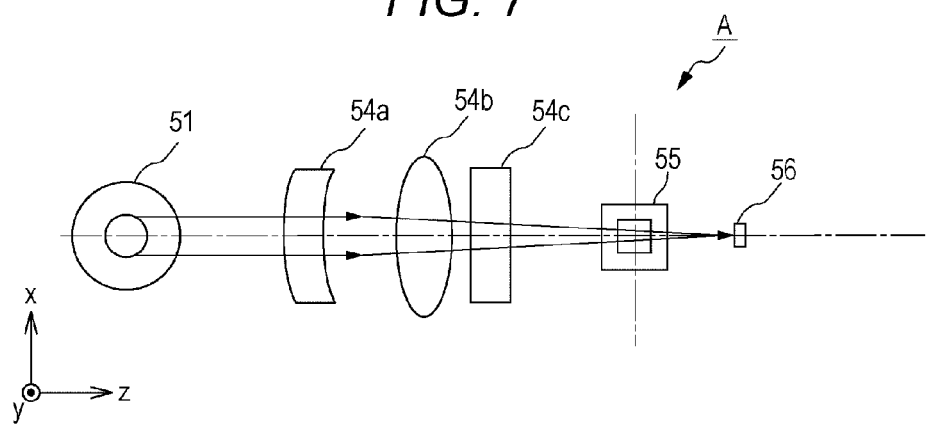
FIG. 7 is a plan view of the optical system relating to the first light source according to the embodiment.

Next, an optical system A relating to the first light source is described in detail. FIG. 6 is a side view of the optical system A relating to the first light source 51 (viewed in x direction). FIG. 7 is a plan view of the optical system A relating to the first light source 51 (viewed in y direction). As illustrated in FIGS. 6 and 7, the optical system A relating to the first light source 51 includes a first lens system 52 having a window 52*a* and a single bi-convex lens (collimeter lens) 52*b*, and an irradiation lens system 54 having a bi-R cylindrical lens 54*a*, a bi-R spherical lens 54*b*, and a bi-R spherical cylindrical lens 54*c*.

As illustrated in FIG. 6, when the laser light emitted from the first light source 51 is viewed from one side (x direction), the diffusing laser light emitted from the first light source 51 is finally concentrated on the specimen flow flowing in the flow cell 55 by the b-R cylindrical lens 54*a* and the bi-R spherical lens 54*b*.

As illustrated in FIG. 7, when the laser light emitted from the first light source 51 is viewed from an upper side (y direction), the diffusing pulse laser light emitted from the first light source 51 is collimated by the window 52*a* and then enters the single bi-convex lens 52*b* to be converted into parallel ray. The resulting parallel ray is then reflected by the dichroic mirror 53 and concentrated on the light blocking board 56 behind the flow cell 55 by the bi-R cylindrical lens 54*a*, bi-R spherical lens 54*b*, and bi-R spherical cylindrical lens 54*c*.

Figure 8:
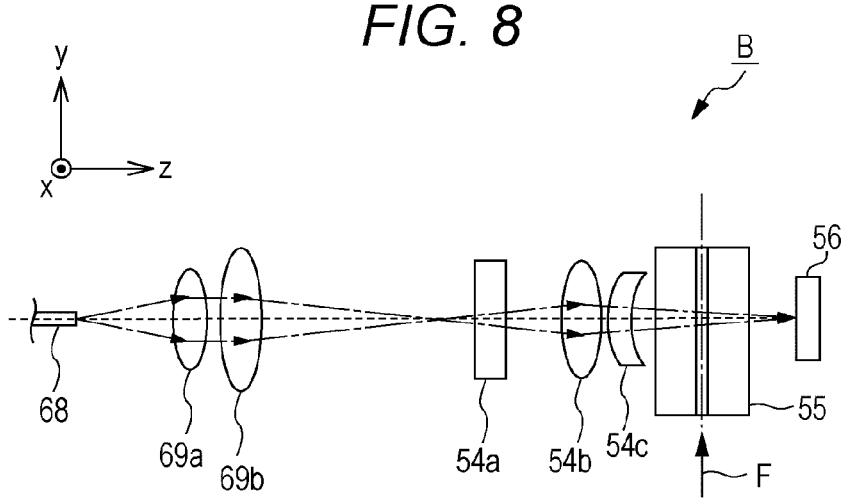
FIG. 8 is a side view of an optical system relating to a second light source according to the embodiment.
Figure 9:
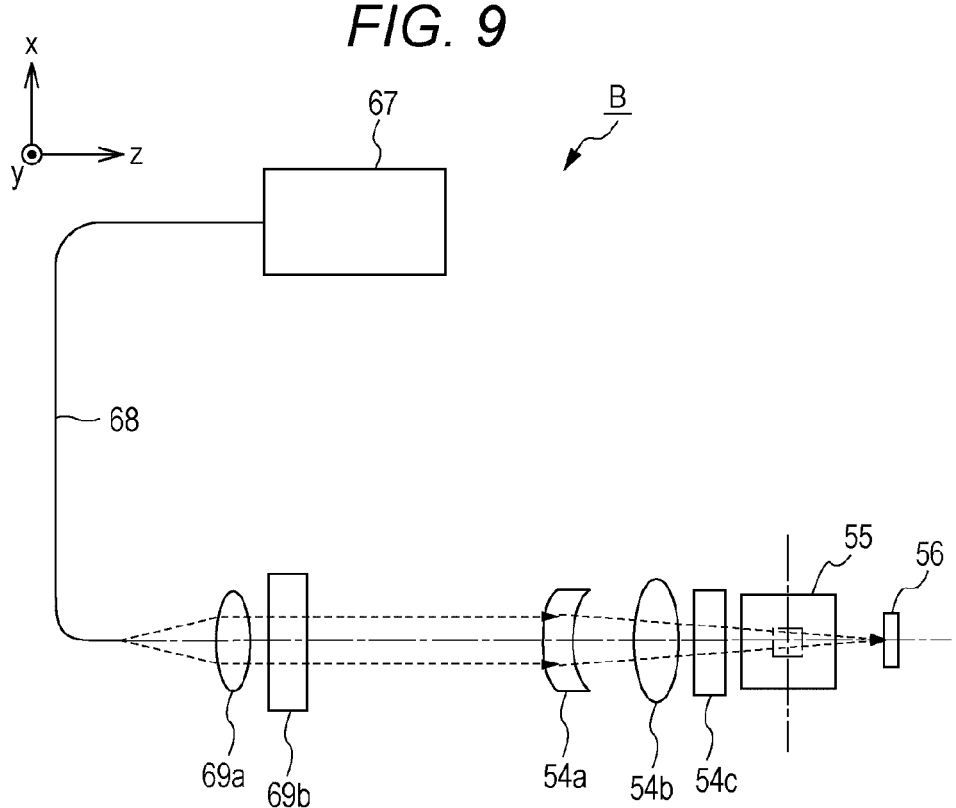
FIG. 9 is a plan view of the optical system relating to the second light source according to the embodiment.

Next, an optical system B relating to the second light source 67 is described in detail below. FIG. 8 is a side view of the optical system B relating to the second light source 67 (viewed in x direction). FIG. 9 is a plan view of the optical system B relating to the second light source 67 (viewed in y direction). As illustrated in FIGS. 8 and 9, the optical system B relating to the second light source 67 includes a second lens system 69 having a single bi-convex lens 69a and a planoconvex cylindrical lens 69b, and an irradiation lens system 54 having a bi-R cylindrical lens 54a, a bi-R spherical lens 54b, and a bi-R spherical cylindrical lens 54c.

As illustrated in FIG. 8, when the pulse laser light emitted from the optical fiber flux 68 is viewed from one side (x direction), the diffusing pulse laser light emitted from the optical fiber flux 68 is converted into parallel ray on the single bi-convex lens 69a. The resulting parallel ray is converged in a direction F where the measurement specimen flows by the planoconvex cylindrical lens 69b and then diffuses. The diffusing light then passes through the bi-R cylindrical lens 60c, and is concentrated on the light blocking board 56 behind the flow cell 51 by the bi-R spherical lens 54a and the bi-R spherical cylindrical lens 54b.

As illustrated in FIG. 9, when the pulse laser light emitted from the optical fiber flux 68 is viewed from an upper side (y direction), the diffusing pulse laser light emitted from the optical fiber flux 68 enters the single bi-convex lens (collimeter lens) 69a to be converted into parallel ray. The resulting parallel ray passes through the planoconvex cylindrical lens 69b, and is concentrated on the light blocking board 56 behind the flow cell 55 by the bi-R cylindrical lens 54a, bi-R spherical lens 54b, and bi-R spherical cylindrical lens 54c.

Figure 10:
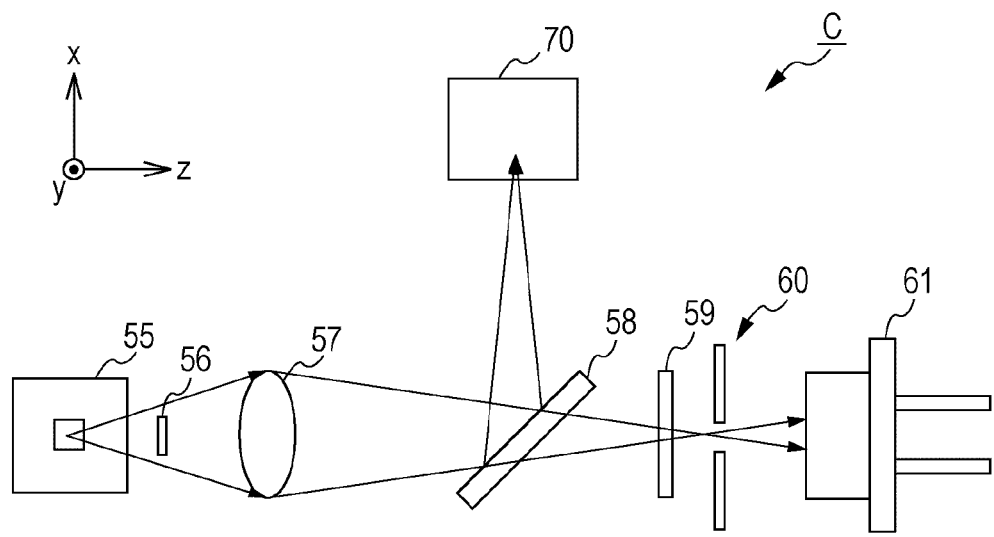
FIG. 10 is a plan view of an optical system relating to an imaging device and a detector according to the embodiment.

Next, an optical system C relating to the photodiode 61 and the camera 70 is described below. FIG. 10 is an upper view of the optical system C relating to the photodiode 61 and the camera 70 (viewed in y direction). The forward scattered light generated from the cell in the specimen flow by the light emitted from the first light source 51 and applied thereto is concentrated by the lens 57a, and transmits through the dichroic mirror 58 and the filter 59 and then passes through the pin hole 60 to enter the photodiode 61. Then, the forward scattered light signal generated from the cell is detected by the photodiode 61.

The scattered light generated from the cell in the specimen flow by the light emitted from the second light source 67 and applied thereto is concentrated by the lens 57a and reflected by the dichroic mirror 58, and then concentrated on the camera 70 (image formation). As described earlier, the direct rays emitted from the first light source 51 and the second light source 67 are blocked by the light blocking board 56. Therefore, the camera 70 can capture the cell image with the direct ray from the second light source 67 completely blocked (dark-field illumination). The image thus captured shows the cell in white with background in black.

Figure 11:
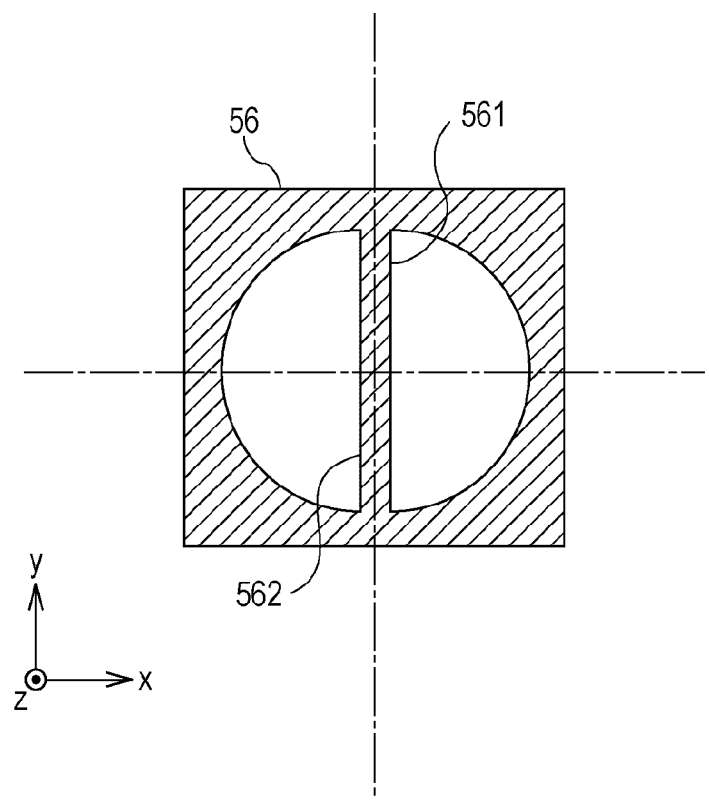
FIG. 11 is an illustration of a light blocking board according to the embodiment.

FIG. 11 is an illustration of the light blocking board 56. As illustrated in FIG. 11, the light blocking board 56 has a circular opening 562 formed in a center portion thereof, wherein a light blocking portion 561 is formed at the center of the circular opening 562. The light blocking portion 561 extends in a direction parallel in with the specimen flow (y direction) to longitudinally traverse the circular opening 562. The light blocking portion 561 has a small width in a direction perpendicular to the specimen flow (x direction). According to the structure, the direct rays from the first light source 52 and the second light source 67 are blocked by the light blocking portion 561. The scattered light generated from the cell in the specimen flow enters the lens 57a through the circular opening 562 of the light blocking board 56. The light blocking board 56 can be easily formed by, for example, processing a metal board painted in black.

[Details of Characteristic Parameters]

<Characteristic Parameters Used to Categorize Target Cells to be Analyzed>

The measurement specimen may include, other than target cells to be analyzed, mucus, blood residue, debris such as cell fragments, and white blood cells (hereinafter, may be collectively called "debris"). In the case where the measurement specimen includes a large quantity of debris, fluorescence from the debris is detected as noise, which adversely affects the accuracy of measurement. According to the present embodiment, therefore, the signal processing circuit 4 obtains from the forward scattered light signal outputted from the photodiode 55 a plurality of characteristic parameters on which sizes of particles including target cells to be analyzed are reflected, which are a signal waveform pulse width of the forward scattered light (FSCW) and a signal waveform peak value of the forward scattered light (FSCP).

The signal waveform peak value of the forward scattered light (FSCP) represents a maximum intensity of the detected forward scattered light. The signal waveform pulse width of the forward scattered light (FSCW) represents a signal waveform width of the forward scattered light having a larger intensity than baseline. The system controller 13 receives the forward scattered light data including the signal waveform pulse width of the forward scattered light (FSCW) and the signal waveform peak value of the forward scattered light (FSCP) from the apparatus body 12 by way of the external communication controller 25. The system controller 13 then creates a scattergram using the signal waveform pulse width of the forward scattered light (FSCW) and the signal waveform peak value of the forward scattered light (FSCP), and differently categorizes target cells to be analyzed and particles other than the target cells to be analyzed (for example, debris).

The debris is smaller than the target cell to be analyzed. Therefore, the signal waveform peak value of the forward scattered light (FSCP) and the signal waveform pulse width of the forward scattered light (FSCW) of the debris, which respectively indicate a particle size, are smaller than the same values of the target cell to be analyzed. Therefore, whether or not the analyzed cell is abnormal can be more accurately determined by selecting the cells having the FSCPG and FSCW values respectively within predetermined ranges as cells to be thereafter analyzed.

<Characteristic Parameters Used to Categorize Non-agglutinated Cell and Agglutinated Cell>

In the present embodiment, the photomultiplier 66 detects the fluorescent light from the measurement specimen flowing in the flow cell 55, and the signal processing circuit 4 obtains the signal waveform peak value (PEAK) of the fluorescent light signal which reflects the height of the signal waveform from the fluorescent light signal outputted from the photomultiplier 66 as a plurality of characteristic parameters and also obtains a differential integrated value (DIV) of the signal waveform which reflects a value indicating a ridge length of the signal waveform. The peak value (PEAK) of the fluorescent light signal waveform represents a maximum intensity of the detected fluorescent light, and the differential integrated value (DIV) of the florescent light signal waveform represents a length of the fluorescent light signal waveform having an intensity larger than a reference value.

The system controller 13 receives the side fluorescent light data including the differential integrated value (DIV) of the fluorescent light signal waveform and the peak value (PEAK)

of the fluorescent light signal waveform by way of the external communication controller 25, and compares a value obtained by dividing the differential integrated value (DIV) of the fluorescent light signal waveform by the peak value (PEAK) of the fluorescent light signal waveform (DIV/PEAK) to a given threshold value to determine whether the cell is an agglutinated cell or a non-agglutinated cell.

The differential integrated value is obtained by differentiating the signal waveforms and summing absolute values thereby obtained. The differential integrated value of a signal with no valley in its waveform is substantially equal to twice a peak value of the signal. On the other hand, the differential integrated value of a signal having any valleys in its waveform is larger than twice a peak value of the signal. The more valleys the waveform has and the deeper the valleys are, there is a larger difference between the differential integrated value and twice the peak value.

In view of a noise possibly superposed on a signal, the system controller 13 uses "2.6", slightly larger than "2", as the "given threshold value" which is used as a reference value for determining whether the target cell to be analyzed is an agglutinated cell or a non-agglutinated cell. The given threshold value is not necessarily limited to 2.6, however, should preferably be as close to 2.0 as possible. When the value obtained by dividing the differential integrated value (DIV) of the fluorescent light signal waveform by the peak value (PEAK) of the fluorescent light signal waveform (DIV/PEAK) is larger than the given threshold value, there is at least a valley in the waveform of the fluorescent light signal. Accordingly, the target cell to be analyzed can be categorized as an agglutinated cell where multiple cells are agglutinated. The signal waveform of the fluorescent light shows a more distinct peak and valley than the signal waveforms of the forward scattered light and the side scattered light. When the signal waveform of the fluorescent light is used, therefore, agglutinated/non-agglutinated cells can be more accurately discriminated.

<Characteristic Parameters Used to Categorize DNA Quantity Abnormal Cell>

When a normal cell is transformed into a cancer cell, cell division becomes more aggressive, increasing a DNA quantity of the cell as compared to that of the normal cell. Therefore, the DNA quantity can be used as an indicator for determining canceration or atypia of the cell. As a value which reflects the nuclear DNA quantity can be used a pulse area of the fluorescent light signal generated from the target cell to be analyzed on which the laser light is applied (fluorescence quantity) (SFLI). The pulse area of the fluorescent light signal (fluorescence quantity) (SFLI) represents an area of a portion surrounded by a reference value and the fluorescent light signal waveform. The signal processing circuit 4 obtains the pulse area of the fluorescent light signal (fluorescence quantity) (SFLI) indicating the value of the nuclear DNA quantity of the target cell to be analyzed from the fluorescent light signal outputted from the photomultiplier 66 as the characteristic parameter. Then, the system controller 13 determines whether the fluorescence quantity is equal to or greater than a given threshold value, and categorizes the cell as a DNA quantity abnomial cell having an abnormal DNA quantity when the fluorescence quantity is equal to or greater than the given threshold value.

To categorize the DNA quantity abnormal cell in the present embodiment, any cells showing the fluorescence quantity equal to 2.5 times or greater than a largest fluorescence quantity of a fluorescent light signal obtained from a standard specimen are determined as the DNA quantity abnormal cells.

<Discrimination of Abnormal Cells>

It is reckoned that when at least two agglutinated cells pass through a beam spot of the laser light, the fluorescent light is emitted from a plurality of nucleuses and detected by the photomultiplier 66, and the pulse accordingly outputted has a relatively large area. As described earlier, however, the present embodiment can effectively omit any data based on the agglutinated cells with a high accuracy by using the value obtained by dividing the differential integrated value of the fluorescent light signal waveform by the peak value (DIV/PEAK). The present embodiment thus characterized can omit any cells determined as the agglutinated cells from all of the cells categorized as the DNA quantity abnormal cells to finally discriminate any truly abnormal cells. This technical advantage can prevent any cell measured as having a large DNA quantity only because it is an agglutinated cell from being miscategorized as an abnormal cell.

[Cell Analyzing Method]

Below is described a cell analyzing method in which the cell analyzing apparatus 10 (see FIG. 1) is used. First, a user manually prepares the measurement specimen to be supplied to the flow cell. More specifically, the measurement specimen is prepared through conventional processes performed by the user to the cells (epithelial cells) collected from a patient's uterine cervix, such as centrifugation (thickening), attenuation, agitation, and PI staining. Then, the user puts the prepared specimen in a test tube (not illustrated in the drawings) and places the test tube at a position beneath a pipette (not illustrated in the drawings) of the apparatus body.

Figure 12:
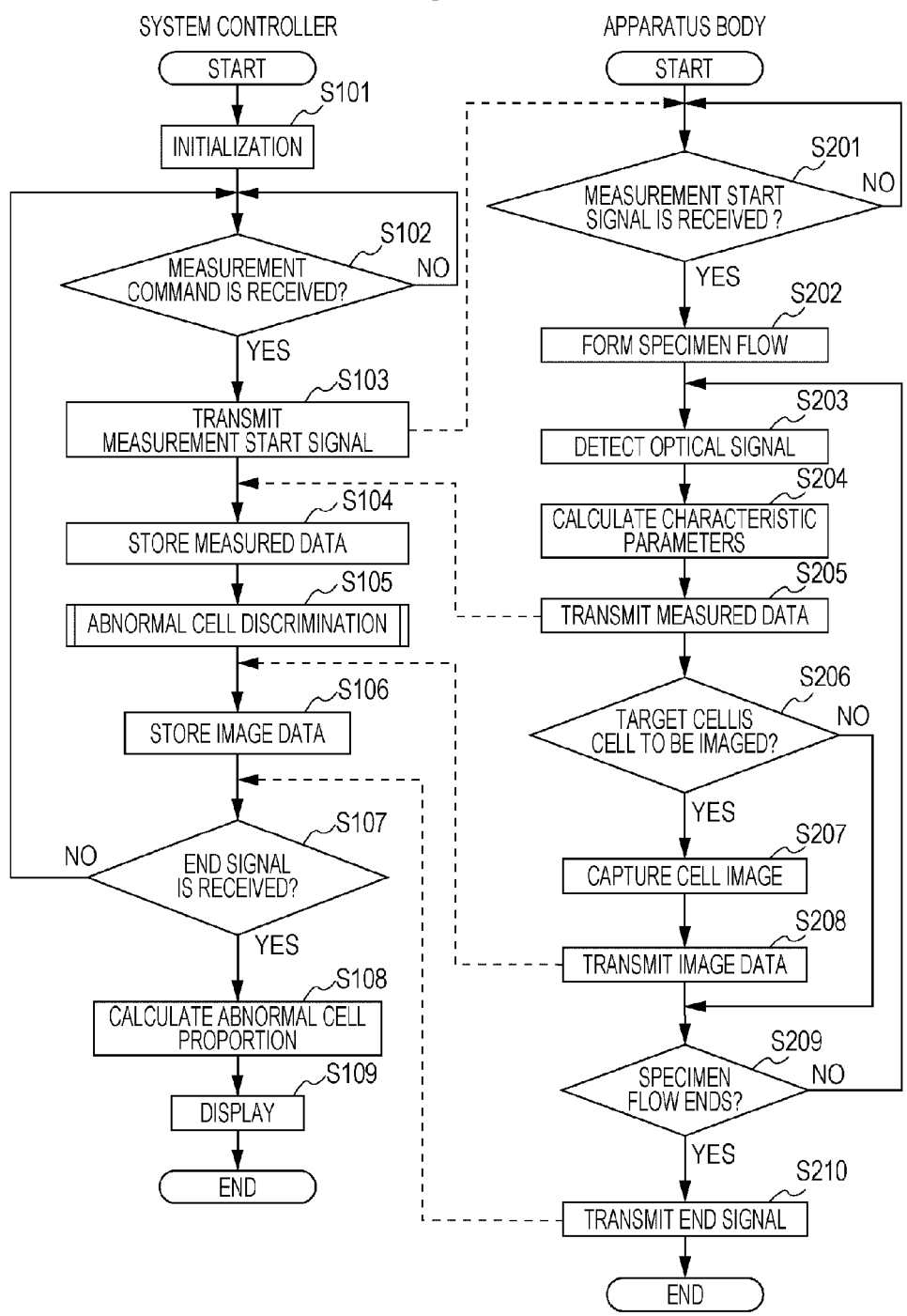
FIG. 12 is a flow chart illustrating processing steps carried out by a CPU of the system controller according to the embodiment.

Next, processing steps carried out by the system controller 13 and the apparatus body 12 are described referring to FIGS. 11 and 12. When the system controller 13 is turned on, the CPU 27a of the system controller 13 initializes the computer program stored in the system controller 13 (Step S101). Then, the CPU 27a determines whether a measurement command is received from a user (Step S102). When determined that the measurement command was received (YES in Step S102), the CPU 27a transmits a measurement start signal to the apparatus body 12 by way of the I/O interface 27f (Step S103).

When the measurement start signal transmitted from the system controller 13 is received by the measurement controller 16 of the apparatus body 12 (Step S201), the measurement specimen retained in the test tube is suctioned therefrom through the pipette and supplied to the flow cell 55 in the apparatus body 12 so that the specimen flow is formed (Step S202). The laser light is applied to the cells in the measurement specimen flowing in the flow cell 55. Then, the forward scattered light emitted from the cell is detected by the photodiode 61, the side scattered light therefrom is detected by the photomultiplier 64, and the side fluorescent light therefrom is detected by the photomultiplier 66 (Step S203).

The forward scattered light signal, side scattered light signal, and side fluorescent light signal outputted from the optical detector 3 are transmitted to and processed by the signal processing circuit 4 in a predetermined manner. As a result, the forward scattered light data (FSC), side scattered light data (SSC), and side fluorescent light data (SFL) are obtained, and the characteristic parameters of these data described earlier are also obtained (Step S204). The obtained characteristic parameters are stored in the storage 21. The measurement controller 16 transmits the obtained characteristic parameters to the system controller 12 as measured data (Step S205).

Then, the measurement controller 16 determines whether the cell is a target cell to be imaged (Step S206). As far as the FSCW and FSCP of the cell stay within the predetermined ranges, the cell is determined as a target cell to be imaged.

When determined in Step S206 that the cell is not a target cell to be imaged (NO in Step S206), the measurement controller 16 jumps the processing to Step S209.

When determined that the cell is a target cell to be imaged (YES in Step S206), the measurement controller 16 implements the imaging operation (Step S207). To capture the image, the light is emitted from the light source 67, and the camera 70 fetches the image of the cell in the flow cell 55 illuminated by the emitted light. Then, the measurement controller 16 implements the transmission of image data of the cell to the system controller 13 by way of the external communication controller 25 (Step S208).

Then, the measurement controller 16 determines whether the specimen flow flowing in the flow cell 51 ends (Step S209). In the case where the flow already ended, the measurement controller 16 transmits information indicating the ended flow (end signal) to the system controller 13 (Step S210). In the case where the specimen flow is still ongoing, the measurement controller 16 returns to the processing step of S203.

The CPU 27a of the system controller 12 receives the measured data transmitted from the measurement controller 16, and stores the received measured data in the hard disc 27d (Step S105). The CPU 27a of the system controller 12 performs the abnormal cell discrimination based on the received characteristic parameters of the particle.

Figure 13:
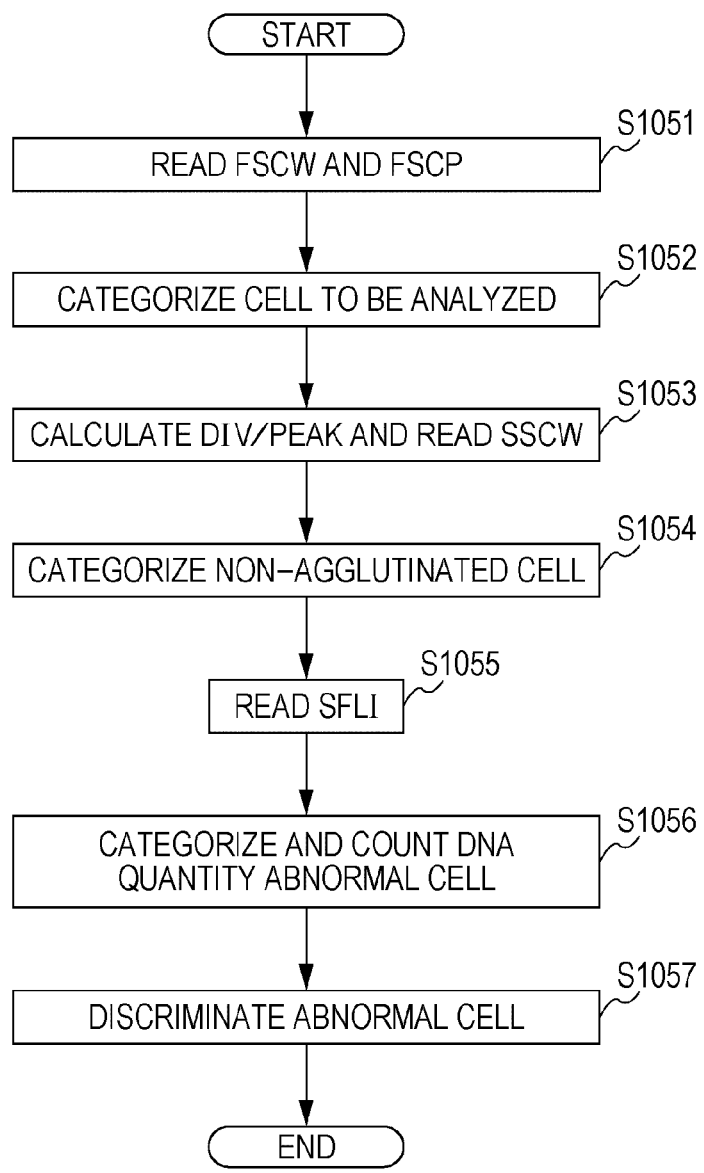
FIG. 13 is a flow chart illustrating cell analyzing steps carried out by the CPU of the system controller according to the embodiment.

To start with, of all of the characteristic parameters of the forward scattered light data of the cell received from the apparatus body 12, the CPU 27a reads out the signal waveform pulse width of the forward scattered light (FSCW) and the signal waveform peak value of the forward scattered light (FSCP) from the hard disc 27d into the RAM 27c (Step S1051 in FIG. 13). The CPU 27a then determines whether the cell is a target cell to be analyzed (Step S1052). As far as the signal waveform pulse width of the forward scattered light (FSCW) and the signal waveform peak value of the forward scattered light (FSCP) of the cell stay within the predetermined ranges, the CPU 27a categorizes the cell as a cell to be analyzed. Otherwise, the CPU 27a determines that the cell is not a target cell to be analyzed but is debris, and omits the cell.

Of all of the characteristic parameters of the side fluorescent light data of the target cell to be analyzed, the CPU 27a reads out the differential integrated value (DIV) of the fluorescent light signal waveform and the peak value (PEAK) of the fluorescent light signal waveform from the hard disc 27d into the RANI 27c to obtain the value calculated by dividing the differential integrated value (DIV) of the fluorescent light signal waveform by the peak value (PEAK) of the fluorescent light signal waveform (DIV/PEAK). Further, of all of the side scattered light data of the target cell to be analyzed, the CPU 27a reads the signal waveform pulse width of the side scattered light (SSCW) from the hard disc 27d into the RAM 27c (Step S1053). The signal waveform pulse width of the side scattered light (SSCW) represents a signal waveform width of the side scattered light having an intensity greater than baseline.

The CPU 27a then compares the value calculated by dividing the differential integrated value (DIV) of the fluorescent light signal waveform by the peak value (PEAK) of the fluorescent light signal waveform (DIV/PEAK) to the threshold value 2.6 to categorize the cell as an agglutinated cell or a non-agglutinated cell (Step S1054). The cell is a non-agglutinated cell when the following formula 1) is met, while the cell is an agglutinated cell otherwise.

$$DIV/PEAK \leq 2.6 \tag{1}$$

Then, the CPU 27a reads out the fluorescence quantity (SFLI) indicating the pulse area of the fluorescent light signal, which is a value reflecting the nuclear DNA quantity of the cell categorized as a non-agglutinated cell in Step S1054, from the hard disc 27d into the RAM 27c as the characteristic parameter of the side fluorescent light data (Step S1055). The hard disc 27d stores therein the fluorescence quantity of the fluorescent light signal of the standard specimen as well, which is also read out from the hard disc 27d into the RAM 27c.

Next, the CPU 27a determines whether the fluorescence quantity (SFLI) of the cell categorized as a non-agglutinated cell is equal to 2.5 times or greater than the fluorescence quantity of the standard specimen (SFLIP), in other words, whether the following formula 2) is met.

$$SFLI \leq SFLIP \cdot 2.5 \tag{2}$$

When determined that the formula (2) is met, the CPU 27a categorizes the cell as a DNA quantity abnormal cell having an abnormal nuclear DNA quantity and counts it accordingly (Step S1056). The CPU 27a discriminates the target cell categorized in Step S126 as having an abnormal DNA quantity as an abnormal cell (Step S1057).

Referring to FIG. 12, when the CPU 27a of the system controller 13 receives the image data transmitted from the apparatus body 12 and determines that the received image is an image of the cell discriminated as an abnormal cell in Step S105, the CPU 27a stores the received image in association with the characteristic parameters of the cell of the image in the hard disc 27d (Step S106).

The system controller 13 then determines whether the end signal is received (Step S107). When determined that the end signal was not received (NO in Step S107), the system controller 13 returns to the processing step of S102. When determined that the end signal was received (YES in Step S107), the system controller 13 calculates the proportion of abnormal cells (Step S108).

The proportion of abnormal cells is the proportion of a total number X of abnormal cells obtained in the abnormal cell discrimination in Step S105 to a total number Y of non-agglutinated cells. The total number Y of non-agglutinated cells is obtained by adding the total number X of abnormal cells to a total number Z of normal cells. Therefore, an abnormal cell proportion W is calculated by the following formula (3).

$$W=X/Y \times 100(\%)=X/(X+Z) \times 100(\%) \tag{3}$$

The abnormal cell proportion is a numeral value serving as an indicator for determining whether at least a given number of abnormal cells are present in the measurement specimen analyzed by the cell analyzing apparatus 10. When the abnormal cell proportion is, for example, equal to or greater than 0.1%, the patient can be diagnosed as very likely to have cancer based on at least the given quantity of abnormal cells detected in the specimen.

The abnormal cell proportion W may be calculated by the following formula (4).

$$W=W/Z \times 100(\%) \tag{4}$$

Then, the system controller 13 displays the abnormal cell proportion, image of the abnormal cell, and other information obtained in Step S108 on the display device 28 (Step S109). At the same time, the system controller 13 creates a scattergram using the characteristic parameters obtained in the abnormal cell discrimination. The system controller 13 creates a FSCW-FSCP scattergram in which a lateral axis represents the pulse width (FSCW) and a longitudinal axis represents the peak value (FSCP), and a (DIV/PEAK)-SSCW scattergram in which a longitudinal axis represents the value (DIV/PEAK) obtained by dividing the differential integrated value (DIV) of the fluorescent light signal waveform by the peak value (PEAK) and a lateral axis represents the signal waveform pulse width of the side scattered light signal (SSCW).

Figure 14:
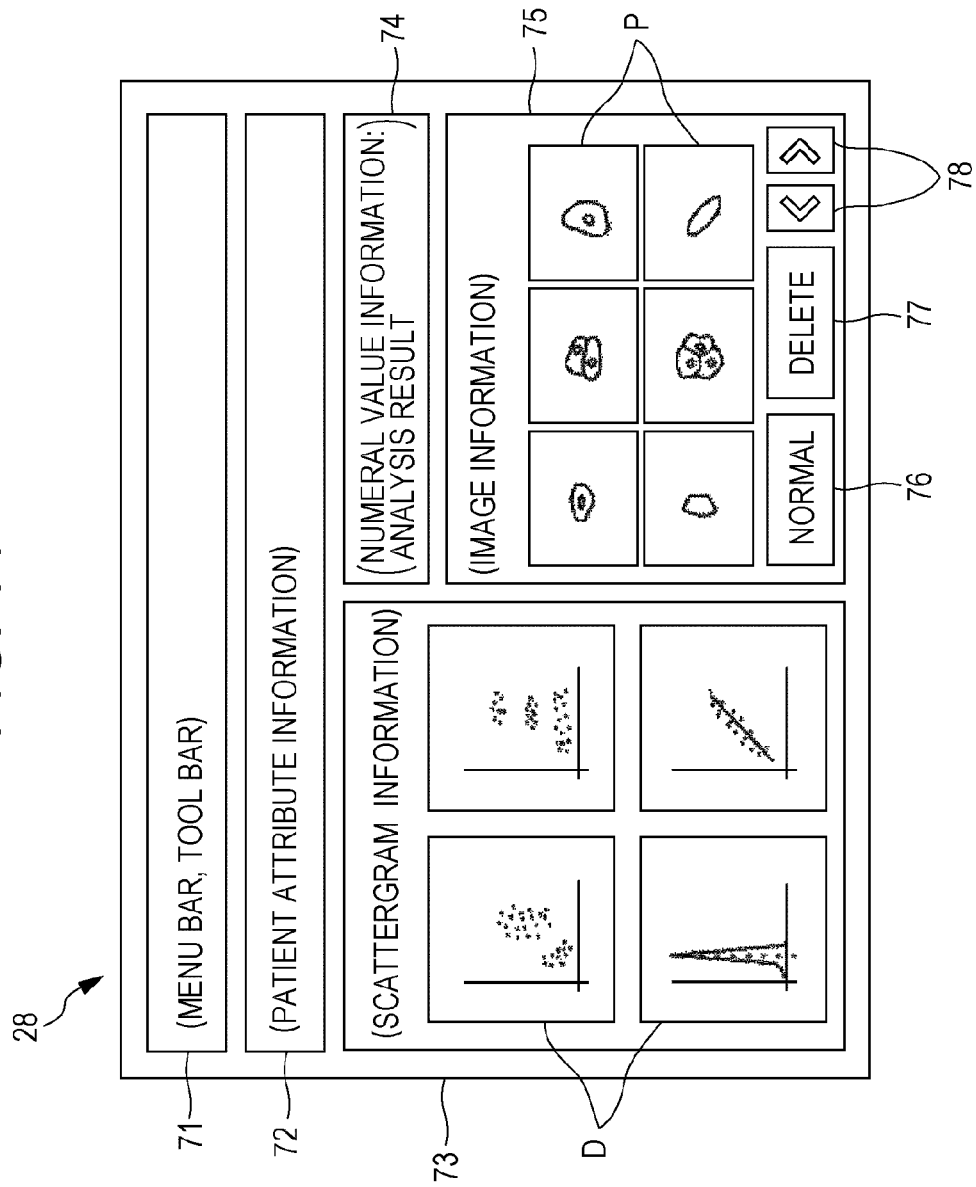
FIG. 14 is a schematic illustration of a screen displayed on a display device according to the embodiment.

FIG. 14 illustrates an example of the image displayed on the display device 28. A display unit 71 which displays a tool bar and a menu bar is provided at the top of the screen of the display device 28, and a patient attribute information display unit 72 which displays attribute-related information of a patient (test subject) such as his or her name and patient ID is provided below the display unit 71. Below the patient attribute information display unit 72 are provided a diagram display unit 73 which displays the scattergrams described earlier and other graphs D, an analysis result display unit 74 which displays the analysis result including the number of abnormal cells and the proportion of abnormal cells, and an image display unit 75 which displays images P of the abnormal cell.

A user can determine whether there is a likelihood that the patient has illness, for example, cancer, by confirming the analysis result displayed on the analysis result display unit 74.

The image display unit 75 can display a plurality of images P at a time (six images in the drawing). A user, for example, a cytotechnologist, can directly confirm with eye the image P of the cell displayed on the image display unit 75 to determine the condition of the cell. The user can confirm whether the cell is truly an abnormal cell by checking the displayed cell image.

The image display unit 75 is provided with a "normal" selection button 76, and a "delete" selection button 77. When the user watches the image P of the cell displayed on the image display unit 75 and determines that the cell image is not the image of an abnormal cell but is the image of a normal cell, the user presses the "normal" selection button 76 while clicking the image P to omit the cell relevant to the image P from the abnormal cells, and then rediscriminates the cell as a normal cell.

In the case where the image P displayed on the image display unit 75 representing neither an abnormal cell nor a normal cell is confirmed as an agglutinated cell or debris (image of the cell not eligible for analysis), the user presses the "delete" selection button 77 while selecting the image P to omit (delete) the cell relevant to the image P from the abnormal cells and normal cells.

The image display unit 75 is provided with a page feed button 78. When the page feed button 78 is pressed, the cell images P are switched forward to the next page or back to the previous page in the image display unit 75 so that the images of all of the abnormal cells can be displayed one by one in the image display unit 75.

According to the embodiment described so far, the light emitted from the first light source 51 to detect the optical signal from the particle and the light emitted from the second light source 67 to capture the particle image are applied to the specimen flow by the irradiation optical system 54. Accordingly, the direct rays of the first light source 51 and the second light source 67 applied to the specimen flow by the irradiation optical system 54 are blocked by the light blocking member to prevent these direct rays from entering the photodiode 61 and the CCD camera 70. When the direct rays are thus blocked to capture the particle image (dark-field illumination), background of the image can be darkened. Therefore, a high-contrast image can be obtained from even an optically transparent particle. According to the embodiment described so far, the particle analyzing apparatus can obtain such a high-contrast image from even an optically transparent particle and characteristic parameters of the particle based on at least forward scattered light generated therefrom. The present embodiment is further technically advantageous in that most of the optical devices can be shared by the system for obtaining the particle characteristic parameters and the system for capturing the particle image, thereby miniaturizing the optical system.

According to the embodiment described so far, the imaging device is provided at the position where the direct ray of the second light source is completely blocked by the light blocking member to capture the particle image in the completely dark field. However, the present invention is not necessarily limited thereto. For example, the imaging device may be provided at a position where at least a part of the direct ray from the second light source is blocked by the light blocking member. The suggested structure is described referring to FIG. 15.

Figure 15A:
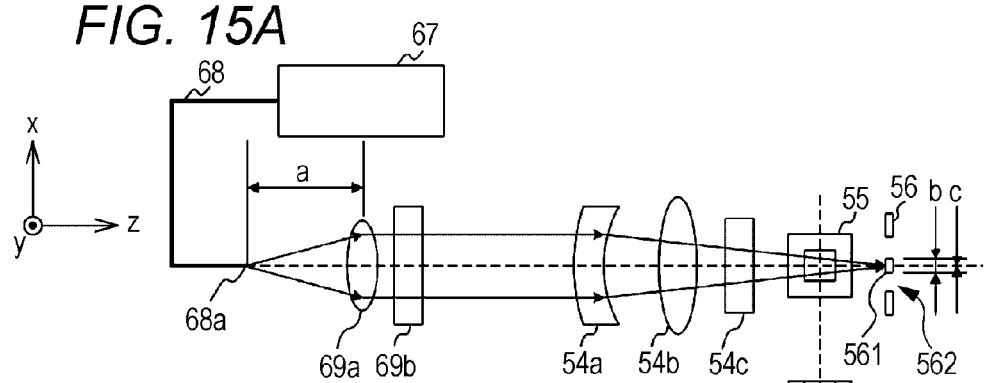
FIG. 15A is a plan view illustrating structural elements of an optical system according to the embodiment 1 of the present invention.
Figure 15B:
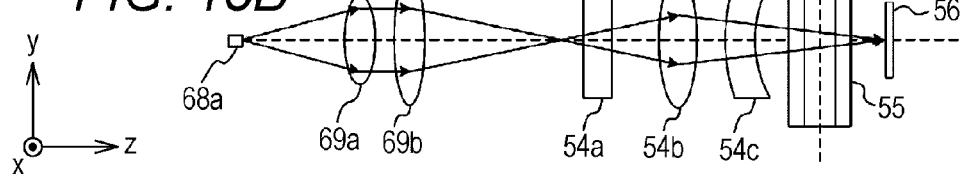
FIG. 15B is a side view illustrating the structural elements of the optical system according to the embodiment 1.
Figure 15C:
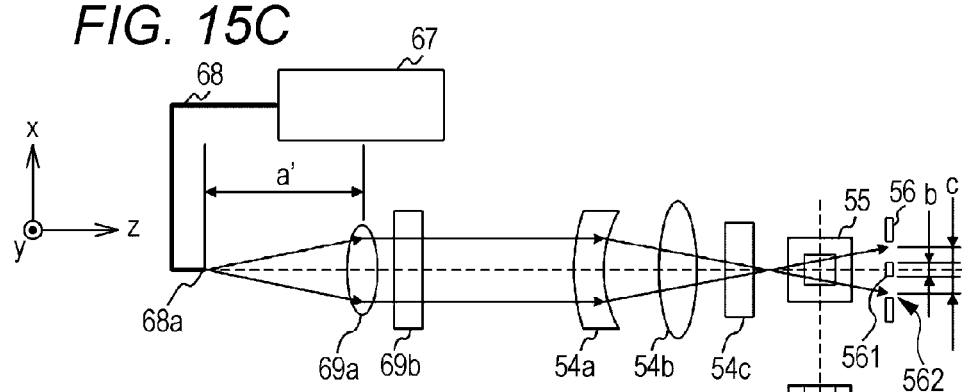
FIG. 15C is a plan view illustrating structural elements of an optical system according to the embodiment 2 of the present invention.
Figure 15D:
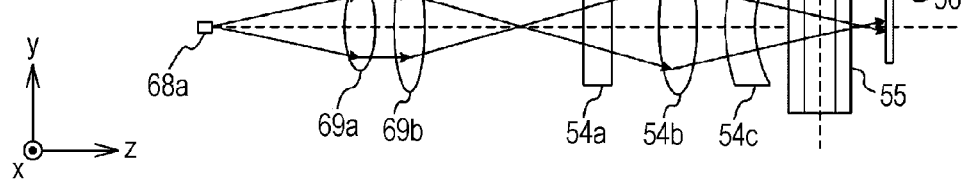
FIG. 15D is a side view illustrating the structural elements of the optical system according to the embodiment 2.

FIGS. 15A-15D illustrate an optical system relating to a second light source according to the embodiment 1 and an optical system relating to a second light source according to the embodiment 2 so that they can be compared. FIG. 15A is a plan view of the optical system according to the embodiment 1. FIG. 15B is a side view of the optical system according to the embodiment 1. FIG. 15C is a plan view of the optical system according to the embodiment 2. FIG. 15D is a side view of the optical system according to the embodiment 2.

As illustrated with arrows in the drawing, the embodiment 1 is technically characterized in that a light emission end 68a of the optical fiber flux 68 is provided so that the direct ray emitted from the optical fiber flux 68 is all converged on the light blocking portion 561 of the light blocking board 56 and thereby prevented from passing through the opening portion 562. There is a distance a between the light emission end 68a of the optical fiber flux 68 and the single bi-convex lens 69a. When the particle image is captured by the camera 70 in the optical system, only the light scattered by the particles enters the camera 70a with the direct ray from the optical fiber flux 68 blocked. Therefore, a particle image with dark background is captured in the completely dark field.

When a width of the light blocking portion 561 in x direction is called b, and an optical width of the direct ray which arrived at the light blocking board 56 in x direction (length of projected image in x direction when light is illuminated at the position of the light blocking board 56) is called c, b and c meets the relationship expressed by b (c. In the embodiment 1, the light is concentrated on the light blocking portion 561. Therefore, c=0.

In the embodiment 2, there is a distance a' (a<a') between the light emission end 68a of the optical fiber flux 68 and the single bi-convex lens 69a. In general, a distance between a lens and a position where an image is formed (position where light is converged) is smaller as a distance between the lens and a light source is larger. According to the embodiment 2, therefore, the direct ray emitted from the optical fiber 68 is converged once at a position on the near side of the light blocking portion 561 and then to diffuse from there as illustrated with arrows in FIG. 15. A part of the diffused direct ray is blocked by the light blocking portion 561, whereas the rest of the direct ray which was not blocked by the light blocking portion 561 transmits through the opening portion 562. When the particle image is captured by the camera 70 in the optical system in this state, background of the obtained image is clearer compared to that of the image obtained in the completely dark field.

When the width of the light blocking portion 561 in x direction is called b, and the optical width of the direct ray which arrived at the light blocking board 56 in x direction is called c, which satisfy the relationship expressed by b<c.

When a part of the direct ray is thus blocked by the light blocking portion 561, the image background can have different levels of brightness. The brightness of the background can be quantitatively adjusted by changing the proportion between b and c. More specifically, the completely dark field can be obtained when c/b is set to 0 (c/b $\langle$ 1, and background of the obtained image is clearer compared to that of the image captured in the completely dark field when c/b is set to 1 (c/b. When c/b is further larger than 1, the background thereby obtained can be even brighter. In the case where the light blocking portion 561 is removed (b=0) or the width of the light blocking portion 561 is too small, the direct ray of the first light source 51 entering the photodiode 71 makes it difficult to detect the forward scattered light. Therefore, the c/b proportion is preferably in the range of 1<c/b<17 to obtain an image with brighter background. To intentionally create a rather dark-field photographing condition, c/b=2 is a preferable example. To intentionally create a rather bright-field photographing condition, c/b=4 is a preferable example.

As described earlier referring to the drawings, the b/c proportion can be adjusted by arbitrarily changing the distance between the light emission end 68a of the optical fiber flux 68 and the single bi-convex lens 69a.

Figure 16:
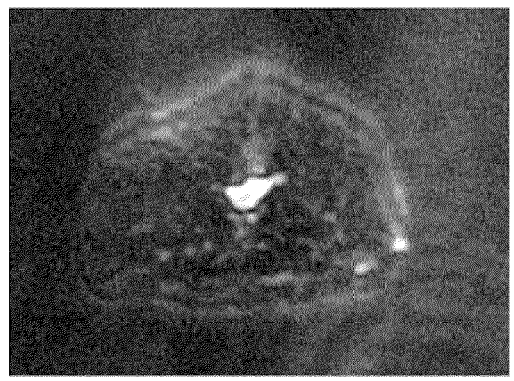
FIG. 16 shows a captured cell image.
Figure 17:
FIG. 17 shows a captured cell image.
Figure 18:
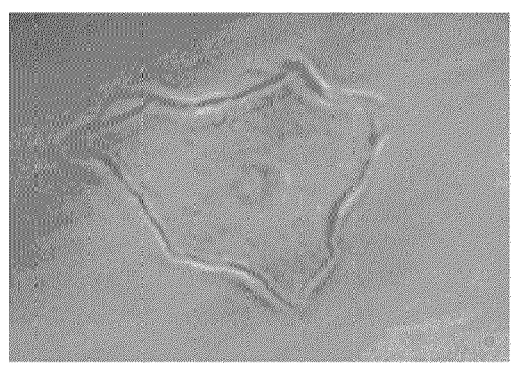
FIG. 18 shows a captured cell image.

FIGS. 16-18 are images of epithelial cells photographed by the particle analyzing apparatus. FIG. 16 is an image obtained in the completely dark field (c/b=0) according to the embodiment 1. FIG. 17 is an image obtained in the rather dark field (c/b=2) according to the embodiment 2. FIG. 18 is an image obtained in the rather bright field (c/b=4) according to the embodiment 2.

As illustrated in FIG. 16, the image photographed in the completely dark field, even if it is obtained from the optically transparent epithelial cell, has a bright nucleus with dark background. Thus, a high-contrast image can be obtained.

As illustrated in FIG. 17, the image photographed in the rather dark field has less dark background than the image captured in the completely dark field.

As illustrated in FIG. 18, the image photographed in the rather bright field has brighter background than the image captured in the rather dark field.

When the image is captured in the rather dark field or rather bright field as illustrated in FIGS. 16b and 16c, the nucleus is less bright, slightly degrading the contrast as compared to the image captured in the completely dark field. However, in the image thus obtained where the background is brightened, the interior of the cell other than the nucleus can be easily confirmed with eye.

In the embodiment 2, the distance between the light emission end 68a of the optical fiber flux 68 and the single bi-convex lens 69a is increased as compared to the embodiment 1 to make a part of the direct ray from the optical fiber flux 68 enter the camera 70 through the circular opening 562. However, the present invention is not limited thereto. For example, the width b of the light blocking portion 561 may be reduced, the light blocking board 56 may be more distant from the optical fiber flux 68 than the position according to the embodiment 1 (displaced to the downstream side in z direction in FIG. 15), or the bi-R cylindrical lens 54a may be closer to the optical fiber flux 68 than the position according to the embodiment 1 (displaced to the upstream side in z direction in FIG. 15). According to the structure, the direct ray emitted from the optical fiber flux 68 is converged on the near side of the light blocking portion 561, and the width of the light arriving at the light blocking board 561 is increased. As a result, a part of the direct ray is made to enter the camera 70 through the circular opening 562.

The embodiments disclosed herein are illustrative and should not be construed as being restrictive in all aspects. The scope of the invention is defined by the scope of the claims rather than by the description of the embodiment, and all changes that fall within the scope of claims and the scope and meaning of equivalence are encompassed herein.

The embodiment determines whether at least the given quantity of abnormal uterocervical cells are present in the measurement specimen collected from a test subject. However, the cell analyzing apparatus according to the present invention is not limited thereto, and can be used to determine whether the measurement specimen collected from the test subject includes a given quantity of abnormal cells in hemocyte cells, urine cell components, epidermal cells of oral cavity, bladder, or pharynx, or any other organs.

In the abnormal cell discrimination according to the embodiment, whether the cell is a DNA quantity abnormal cell is determined after whether the cell is a non-agglutinated cell or an agglutinated cell is determined, which, however, may be reversed. The characteristic parameters used in the abnormal cell discrimination are not particularly limited to those described in the embodiment.

In the embodiment, the measurement controller 16 of the apparatus body 12 obtains the characteristic parameters from the optical signals and transmits the obtained characteristic parameters of the particle to the system controller 13, and the CPU 27 of the system controller 13 performs the abnormal cell discrimination based on the received characteristic parameters. However, the present invention is not necessarily limited thereto. For example, the measurement controller 16 of the apparatus body 12 may obtain the characteristic parameters of the particle and perform the abnormal cell discrimination based on the obtained characteristic parameters.

In the embodiment, the measurement controller 16 of the apparatus body 12 determines in Step S206 that the cell is a target cell to be imaged when the FSCW and FSCP of the cell stay within the predetermined ranges. However, the present invention is not necessarily limited thereto. For example, the target cell may be determined as a target cell to be imaged when the formula 1) or the formula 2) is met. The fluorescence quantity of the fluorescent light signal in the standard specimen is also stored in the storage 21.

In the embodiment, the numeral value information (analysis result) and the scattergrams are displayed as well as the abnormal cell image. These data are not necessarily displayed on the display device but may be printed on paper.

According to the embodiment, the measurement specimen including cells collected from an test subject's uterine cervix is analyzed by the cell analyzing apparatus. The present invention is not necessarily limited thereto. A measurement specimen including urine cell components collected from a test subject may be analyzed by a urine cell component analyzing apparatus.

In the embodiment, the pulse laser light source which emits the pulse beam is used as the second light source 67. However, the present invention is not necessarily limited thereto. For example, a continuum laser light source may be used as the second light source 67.

In the embodiment, the first lens system 52 does not include a cylindrical lens. However, the present invention is not necessarily limited thereto. For example, the first lens system 52 may include a cylindrical lens.

What is claimed is:

1. A particle analyzing apparatus, comprising:
a flow cell which forms a specimen flow including particles;
first and second light sources;
an irradiation optical system which applies first light emitted from the first light source and second light emitted from the second light source onto the specimen flow;
a detector which detects forward scattered light caused by irradiation of the first light onto the particles in the specimen flow, and generates a signal according to the detected forward scattered light;
a controller which obtains characteristic parameters of the particles based on the signals from the detector;
an imaging device which captures images of the particles in the specimen flow using the second light, and
a single light blocking member which is disposed between the flow cell and the detector, and which is disposed between the flow cell and the imaging device;
wherein
the single light blocking member is disposed so as to block a direct ray of the first light entering into the detector and block at least a part of a direct ray of the second light entering into the imaging device.

2. The particle analyzing apparatus of claim 1, wherein the single light blocking member is disposed so as to completely block the direct ray of the second light entering into the imaging device.

3. The particle analyzing apparatus of claim 1, further comprising
a first optical system which makes the first light enter the irradiation optical system; and
a second optical system which makes the second light enter the irradiation optical system.

4. The particle analyzing apparatus of claim 3, wherein the first optical system makes the first light enter the irradiation optical system as parallel ray in directions perpendicular to and in parallel with the specimen flow, and
the second optical system makes the second light enter the irradiation optical system as parallel ray in the direction perpendicular to the specimen flow, and further makes the second light enter the irradiation optical system as converging ray in the direction in parallel with the specimen flow.

5. The particle analyzing apparatus of claim 3, wherein the irradiation optical system concentrates the first light on the specimen flow in a direction in parallel with the specimen flow and further concentrates the first light at a position where the single light blocking member is disposed in a direction perpendicular to the specimen flow, and the irradiation optical system concentrates the second light at the position where the single light blocking member is disposed in the directions perpendicular to and in parallel with the specimen flow.

6. The particle analyzing apparatus of claim 3, wherein the second optical system and the irradiation optical system respectively include at least a cylindrical lens.

7. The particle analyzing apparatus of claim 3, wherein the single light blocking member has a light blocking portion extending in a direction in parallel with the specimen flow and a circular opening on either side of the light blocking portion.

8. The particle analyzing apparatus of claim 1, further comprising a second detector which detects side scattered light generated from the particles in the specimen flow, and a third detector which detects side fluorescent light generated from the particles in the specimen flow, wherein
the controller obtains characteristic parameters of the particles based on signals from the first, second and third detectors.

9. The particle analyzing apparatus of claim 1, wherein the controller controls the second light source so that the particle is thereby illuminated when a predetermined characteristic parameter is obtained from the particle.

10. The particle analyzing apparatus of claim 1, further comprising a memory, wherein
the controller stores the characteristic parameters obtained from the particles in the memory in association with images of the particles.

11. The particle analyzing apparatus of claim 1, further comprising a display, wherein
the controller controls the display so that at least one of the characteristic parameters obtained from the particles and images of the particles is displayed thereon.

12. The particle analyzing apparatus of claim 1, wherein the particle in the specimen is a cell.

13. The particle analyzing apparatus of claim 1, further comprising:
a dichroic mirror which reflects one of the light from the first light source and the second light source, and transmits through the other of the light from the first light source and the second light source,
wherein the light blocking member is disposed between the flow cell and the dichroic mirror.

14. A particle analyzing apparatus, comprising:
a flow cell which forms a specimen flow including particles;
first and second light sources;
an irradiation optical system which applies first light emitted from the first light source and second light emitted from the second light source onto the specimen flow;
a detector which detects forward scattered light caused by irradiation of the first light onto the particles in the specimen flow, and generates a signal according to the detected forward scattered light;
a controller which obtains characteristic parameters of the particles based on the signals from the detector;
an imaging device which captures images of the particles in the specimen flow using the second light, and
a light blocking board which is disposed between the flow cell and the detector, and which is disposed between the flow cell and the imaging device;
wherein
the light blocking board is disposed so as to block a direct ray of the first light entering into the detector and block at least a part of a direct ray of the second light entering into the imaging device.

* * * * *